(12) United States Patent
Choi

(10) Patent No.: US 6,873,408 B2
(45) Date of Patent: Mar. 29, 2005

(54) PHOTORESIST MIST AUTO DETECTION SYSTEM

(75) Inventor: Willys Choi, Hsin-Chu (TW)

(73) Assignee: Taiwan Semiconductor Manufacturing Co., Ltd., Hsin Chu (TW)

(*) Notice: Subject to any disclaimer, the term of this patent is extended or adjusted under 35 U.S.C. 154(b) by 197 days.

(21) Appl. No.: 10/043,023

(22) Filed: Jan. 8, 2002

(65) Prior Publication Data

US 2003/0128358 A1 Jul. 10, 2003

(51) Int. Cl.[7] .................................................. G01N 21/00
(52) U.S. Cl. ................................... 356/237.1; 356/237.4
(58) Field of Search ........................... 356/237.1–237.5, 356/338, 239.1, 239.7, 630–632; 438/758, 695; 427/240, 336, 294, 385.5, 425; 118/52, 326, 301

(56) References Cited

U.S. PATENT DOCUMENTS

| | | | | |
|---|---|---|---|---|
| 5,939,139 A | * | 8/1999 | Fujimoto | .................... 427/240 |
| 5,993,547 A | * | 11/1999 | Sato | ............................. 118/50 |
| 6,151,487 A | * | 11/2000 | Kim et al. | ................... 455/134 |
| 6,493,078 B1 | * | 12/2002 | Fitzsimmons et al. | ... 356/239.7 |
| 6,613,588 B2 | * | 9/2003 | Nakano et al. | ................ 438/9 |

FOREIGN PATENT DOCUMENTS

| | | | |
|---|---|---|---|
| JP | 404345014 A | * | 12/1992 |
| JP | 40-5217881 A | * | 8/1993 |
| JP | 11-306646 | * | 11/1999 |

* cited by examiner

Primary Examiner—Hoa Q. Pham
(74) Attorney, Agent, or Firm—Tung & Associates

(57) ABSTRACT

A method and system for detecting contaminants during a semiconductor fabrication operation involving a semiconductor-coating device. A beam of laser light is generated from a laser light source attached to at least one coater cup associated with the semiconductor coating device utilized in the semiconductor fabrication operation. The semiconductor fabrication operation may then be automatically terminated in response to detecting the contaminants utilizing the beam of laser light. The laser light source may be configured as one or more laser generators and/or laser detectors. Such a method and system can thus be implemented to detect photoresist (PR) dust, which is scattered during wafer coating operations.

30 Claims, 2 Drawing Sheets

PHOTORESIST MIST AUTO DETECTION SYSTEM

TECHNICAL FIELD

The present invention relates to semiconductor fabrication methods and systems. The present invention also relates to wafer rotation and wafer spin methods and systems utilized in the production of semiconductor-based integrated circuits. The present invention additionally relates to photoresist and solvent dispensing methods and systems thereof. The present invention also relates to methods and systems for detecting contaminants, such as dust, during semiconductor fabrication operations.

BACKGROUND OF THE INVENTION

The manufacture of integrated circuits involves the transfer of geometric shapes on a mask to the surface of a semiconductor wafer. Thereafter, the semiconductor wafer corresponding to the geometric shapes, or corresponding to the areas between the geometric shapes, is etched away. The transfer of the shapes from the mask to the semiconductor wafer typically involves a lithographic process. This includes applying a solution of a pre-polymer solution to the semiconductor wafer, the pre-polymer being selected to form a radiation-sensitive polymer which reacts when exposed to ultraviolet light, electron beams, x-rays, or ion beams, for example. The solvent in the pre-polymer solution is removed by evaporation, and the resulting polymer film is then baked.

The film can be exposed to radiation, for example, ultraviolet light, through a photomask supporting the desired geometric patterns. Soaking the wafer in a developing solution then develops the images in the photosensitive material. The exposed or unexposed areas are removed in the developing process, depending on the nature of the radiation-sensitive material. Thereafter, the wafer is placed in an etching environment, which etches away the areas not protected by the radiation-sensitive material. Due to their resistance to the etching process, the radiation sensitive-materials are also known as photoresists, and the term photoresist is used hereinafter to denote such radiation-sensitive polymers and their pre-polymers.

Thus, when patterning is performed by etching, a resist film mask having a desired pattern is generally formed on a layer to be etched, and the layer is etched by the use of the mask. A resist film for forming a mask is normally formed on a layer to be etched by coating a resist on a wafer using a resist coater and baking the resist. A prior art resist coater for coating a resist on a wafer is explained with reference to FIG. 1. FIG. 1 is a sectional view showing a structure of a prior resist coater of a spin coat type.

As shown in FIG. 1, a resist coater 10 has a wafer holding table 12 for rotating a wafer W around an axis, which can be perpendicular to the wafer W while holding the wafer W with a wafer surface thereof directed upwardly. A resist supply nozzle 14 supplies resist to the wafer W, which may be held on the wafer holding table 12. A coater cup 16 generally surrounds the wafer holding table 12 and the resist-supplying nozzle 14.

The wafer holding table 12 is generally attached on an upper end of a rotation shaft 18 which penetrates a bottom portion of the coater cup 16 and which may be rotated with a rotation device (not shown). The wafer holding table 12 is generally provided on its wafer holding surface with a chuck mechanism for vacuum-sucking the wafer W, and it can be rotated together with the rotation shaft 18 around an axis, which is generally perpendicular to the wafer holding surface.

The coater cup 16 can trap resist particles, which are generally scattered from the wafer W by a centrifugal force due to the rotation of the wafer W. The coater cup 16 generally possesses an outer cup 20 for trapping resist particles which may be scattered in sidewise and upward directions, and an inner cup 22 for guiding resist particles, which can be scattered in a downward direction from the wafer W to a bottom portion of the outer cup 20.

The outer cup 20 has at an upper portion thereof an opening 24 for introducing the resist supply nozzle 14 or the like, and for taking in and taking out the wafer W. Furthermore, the inner cup 22 is generally provided on a lower portion of the outer cup 20, and the inner cup 22 has a cylindrical portion 22a, and an umbrella portion 22b which spreads toward the inside of the coater cup 16 from an upper opening thereof.

The resist supply nozzle 14 can be lowered via the opening 24 of the coater cup 16, and is generally arranged at a position facing a resist coating surface of the wafer W. Also, in order to clean an edge to the back surface of the wafer W, a first cleaning nozzle 26 for spraying rinse agent can be directed toward the edge of the back surface of the wafer W through the bottom portion of the coater cup 16. Furthermore, in order to clean an edge of the surface of the wafer W, a second cleaning nozzle 28 for spraying rinse agent may be directed toward the edge of the wafer W via the upper opening 24 of the coater cup 16. Exhaust pipes 30 are generally connected to an exhaust device (not shown) for exhausting the inside of the coater cup 16, and a drain pipe 32 for exhausting the resist trapped in the coater cup 16 are connected to the bottom portion of the coater cup 16.

FIG. 1 is thus presented for illustrative and background purposes only. In typical prior art coater cup designs a mist generation mechanism may be relied upon. The wafer generally rotates when the photoresist and solvent are dispensed onto the wafer. The photoresist can thus be coat the wafer through wafer spinning techniques. An edge photoresist can be removed through solvent dispensation. Typically, photoresist dust can result from such a semiconductor fabrication operation and normally should be exhausted by a proper airflow. More often than not, however, the dust is splashed back, thereby forming contaminants and other particles, which result in semiconductor defects. When such contaminant or dust piles up, exhaust lines can choke up. Thus, not enough exhaust may result. The semiconductor fabrication devices in question cannot determine whether such "splash back" is the root cause of decreases in exhaust. Such splash back generally results in manufacturing problems and poor semiconductor device yields.

The present inventor has thus concluded, based on the foregoing that a need exists for an improved method and system for checking contaminants, such as dust, during spin coating and other similar semiconductor fabrication operations. If such contaminants can be detected utilizing a non-evasive detection technique, the semiconductor fabrication operation can be automatically halted to prevent further scattering of contaminants, such as photoresist (PR) dust. The present invention thus meets and solves this important need.

BRIEF SUMMARY OF THE INVENTION

The following summary of the invention is provided to facilitate an understanding of some of the innovative features unique to the present invention, and is not intended to be a full description. A full appreciation of the various aspects of the invention can be gained by taking the entire specification, claims, drawings, and abstract as a whole.

It is therefore one aspect of the present invention to provide an improved semiconductor fabrication method and system.

It is another aspect of the present invention to provide an improved method and system for detecting contaminants during semiconductor fabrication operations.

It is also an aspect of the present invention to provide an improved method and system for detecting photoresist (PR) dust scattered during wafer coating operations.

The above and other aspects of the present invention can thus be achieved as is now described. A method and system for detecting contaminants during a semiconductor fabrication operation involving a semiconductor-coating device is described herein. A beam of laser light is generated from a laser light source attached to at least one coater cup associated with the semiconductor coating device utilized in the semiconductor fabrication operation. The semiconductor fabrication operation may then be automatically terminated in response to detecting the contaminants utilizing the beam of laser light.

The contaminants are generally scattered as a result of the semiconductor fabrication operation. The laser light source may comprise a laser generator. The laser light source may also comprise a laser detector. Thus, one or more laser light sources may be configured to aid in the generation and detection of a laser light beam. The laser light source may also comprise one or more laser generators integrated with one or more laser detector. The semiconductor fabrication operation itself may comprise a wafer spin coating operation. The coater cup can comprise a photoresist (PR) cup. The contaminants may comprise photoresist (PR) dust scattered as a result of a wafer spin coating operation.

A laser light can thus be utilized to detected scattered PR dust. The laser generator and laser detector are generally alterable with respect to height and laser setting numbers. When PR dust is detected, the system can stop automatically. The system described herein can be configured on a PR cup thereby preventing PR dust buildup. By utilizing the present invention, improved photo rework rates may result, in addition to improved semiconductor fabrication yields.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate embodiments of the present invention and are not intended to limit the scope of the invention.

Figure 1:
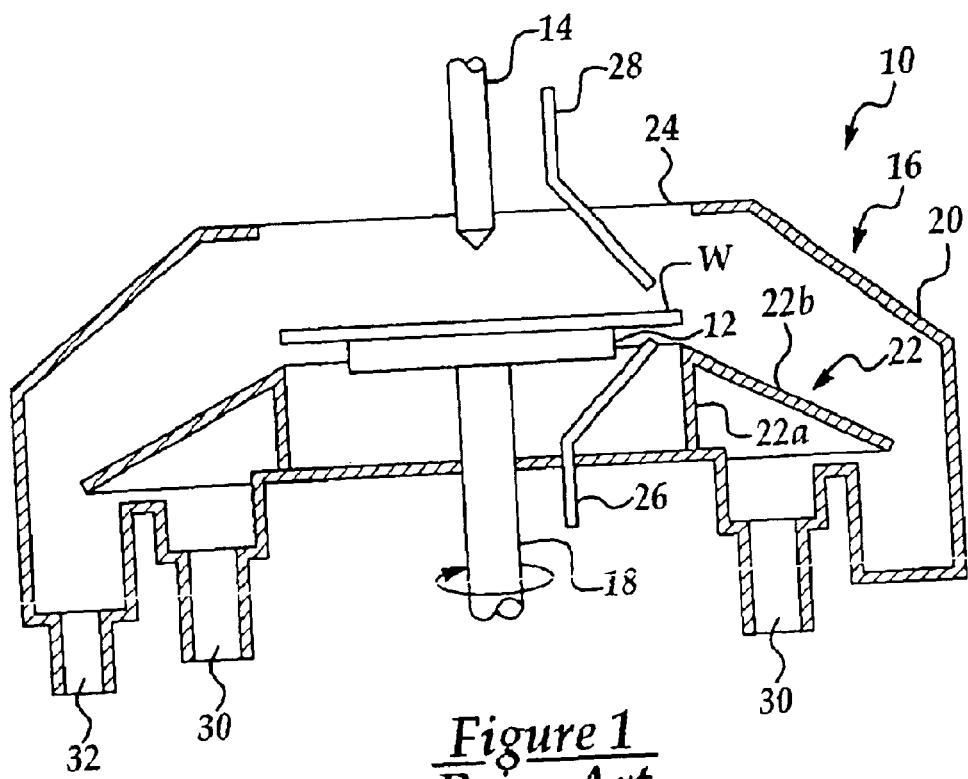
FIG. 1 illustrates a sectional view a prior art resist coater utilized in spin coating operations.
Figure 2:
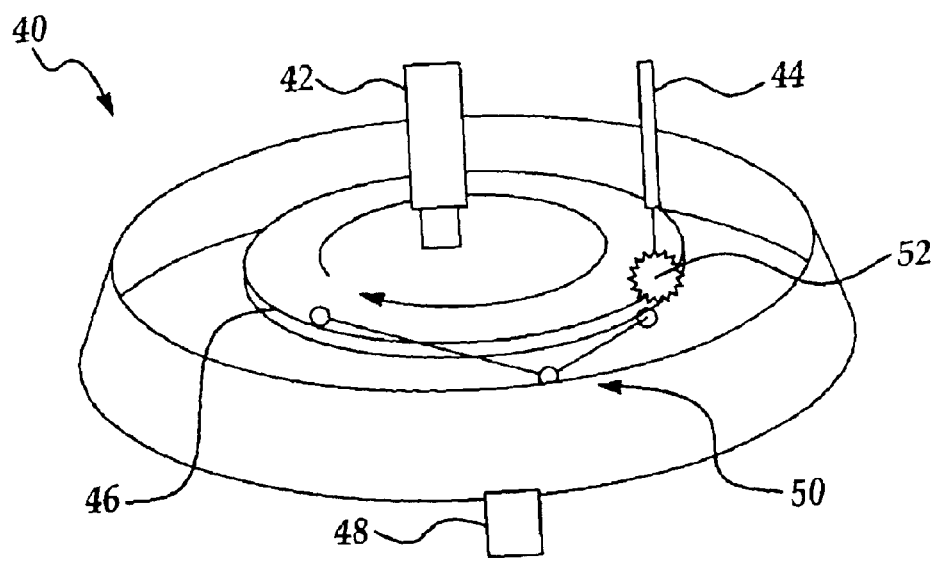
FIG. 2 depicts a pictorial diagram of a prior art coater cup and mist generation mechanism, in accordance with a preferred embodiment of the present invention.

FIG. 2 depicts a pictorial diagram 40 of a prior art coater cup and mist generation mechanism, in accordance with a preferred embodiment of the present invention. Note that the configuration depicted in FIG. 2 is presented herein for illustrative purposes only and is not considered a limiting feature of the present invention. The prior art coater cup and mist generation mechanism illustrated in FIG. 2 generally comprises a solvent nozzle 44 and a photoresist nozzle 42. Solvent photoresist dust 52 is typically generated and scattered during wafer coating operations. The solved photoresist (PR) is often splashed back 50 onto the surface of the wafer 46. Because of the scattering of photoresist (PR) dust or other contaminants, exhaust line 48 can become clogged, resulting in less exhaust availability and eventually, in semiconductor defects and contamination.

In a typical prior art configuration, such as illustrated in FIG. 2, after a photoresist is deposited on wafer 46, the wafer 46 is generally accelerated to create a centrifugal force, which spreads the photoresist toward the edge of the wafer. Wafer 46 may be spun at an intermediate speed for a few seconds before being accelerated to the final high-speed spin. When the bulk of the photoresist reaches the edge of wafer 46, most of the photoresist is flung off in many tiny droplets. It has been shown that while the acceleration rate does not affect the final film thickness, higher acceleration rates do tend to produce more uniform films.

Once wafer 46 is spun up to the final high speed, the wafer continues to spin to cause the photoresist to reach the desired thickness. Photoresist continues to flow outward and off the wafer 46 in concentric waves. Simultaneously, the solvent in the photoresist evaporates quickly because of high convection over the surface of wafer 46. As the solvent fraction in the photoresist decreases, the viscosity of the photoresist gradually increases, causing the outward flow of photoresist to diminish until it almost ceases. Subsequent thinning of the photoresist comes almost entirely from solvent evaporation. When the solvent is mostly evaporated, typically after about 30 seconds, spinning is stopped, and the wafer 46 can be soft baked at a high temperature to evaporate the remaining solvent from the photoresist.

The wafer 46 thus generally rotates when the photoresist and solvent are dispensed onto wafer 46. The photoresist can thus coat wafer 46 through wafer spinning techniques. An edge photoresist can be removed through solvent dispensation. Typically, photoresist dust results from such a semiconductor fabrication operation and normally should be exhausted by a proper airflow. More often than not, however, the dust is splashed back, thereby forming contaminants and other particles, which result in semiconductor defects. When such contaminant or dust piles up, exhaust line 48 can choke up. Thus, not enough exhaust may result. The semiconductor fabrication devices in question cannot determine whether such "splash back" (i.e. splash back 50) is the root cause of decreases in exhaust. Such splash back 50 generally results in manufacturing problems and poor semiconductor device yields.

Figure 3:
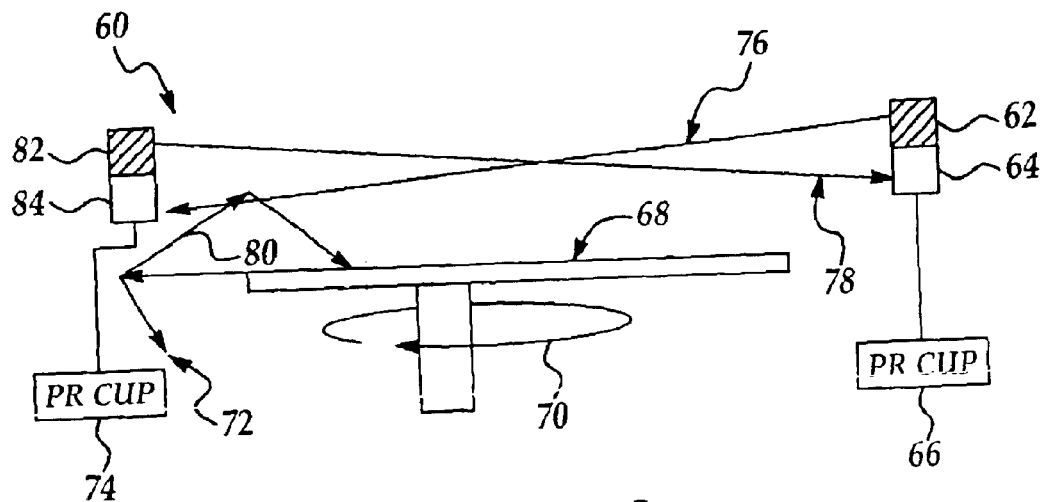
FIG. 3 illustrates a block diagram of a laser generator and detection system, in accordance with a preferred embodiment of the present invention.

FIG. 3 Illustrates a block diagram 60 of a laser generator and detection system, in accordance with a preferred embodiment of the present invention. FIG. 3 thus depicts a wafer 68 which may be utilized during the course of a semiconductor fabrication operation, such as, for example, a wafer spin-coating operation. One or more laser light sources are also indicated in FIG. 3. Such laser light sources are laser generator 62 and laser detector 64, along with laser generator 82 and laser detector 84. Arrow 72 indicates normal photoresist (PR) dust flow, while arrow 80 indicates abnormal PR dust flow.

The wafer can rotate according to a particular rotational direction, as indicated by arrow 70. The aforementioned laser light sources may thus be utilized to detect scattered photoresist (PR) dust during a wafer coating operation. It can be appreciated that although specific laser light sources, such as laser generators 82 and 62 and laser detectors 84 and 64 are illustrated in the configuration depicted in FIG. 3, additional laser light sources may also be utilized in accordance with alternative embodiments of the present invention. Laser generators 82 and 62 and laser detectors 84 and 64 are changeable. That is, the laser generator and laser detector height may be altered in addition to set numbers.

Laser generator 62, for example, can generate a laser light beam 76 which can be detected by a laser detector 84. Likewise, laser generator 82 can generate a laser light beam 78, which can be detected by laser detector 64. Laser generator 62 and laser detector 64 can be attached to a PR cup 66. Similarly, laser generator 82 and laser detector 84 can be attached to a PR cup 74. Each PR cup 74 and 66 can be configured from a transparent material, such as, for example, quartz or glass.

A beam of laser light (e.g., laser light beam 76) can thus be generated from a laser light source (e.g., laser generator 62) attached to at least one coater cup (e.g. PR cup 66) associated with a semiconductor coating device utilized in a semiconductor fabrication operation. The semiconductor fabrication operation may then be automatically terminated in response to detecting contaminants (e.g., PR dust) utilizing the beam of laser light. The contaminants are generally scattered as a result of the semiconductor fabrication operation. The laser light source may comprise a laser generator and/or a laser detector. Thus, one or more laser light sources may be configured to aid in the generation and detection of a laser light beam. The laser light source may also comprise one or more laser generators integrated with one or more laser detectors. The semiconductor fabrication operation itself may comprise a wafer spin coating operation. The contaminants may comprise photoresist (PR) dust scattered as a result of a wafer spin coating operation.

A laser light can thus be utilized to detected scattered PR dust. The laser generator and laser detector are generally alterable with respect to height and laser setting numbers. When PR dust is detected, the system can stop automatically. The system described herein can be configured on a PR cup thereby preventing PR dust buildup. By utilizing the present invention, improved photo rework rates may result, in addition to improved semiconductor fabrication yields. An example of a laser light source that can be implemented in accordance with the method and system of the present invention is a solid state semiconductor light emitter, which are generally known as important devices utilized in diverse applications such as, for example, optoelectronic communication systems and high-speed printing systems. Edge emitting lasers may also be utilized as a laser light source in accordance with the method and system of the present invention. Thus, a variety of types of laser generators and/or laser detectors can be utilized in an implementation of the present invention.

Figure 4:
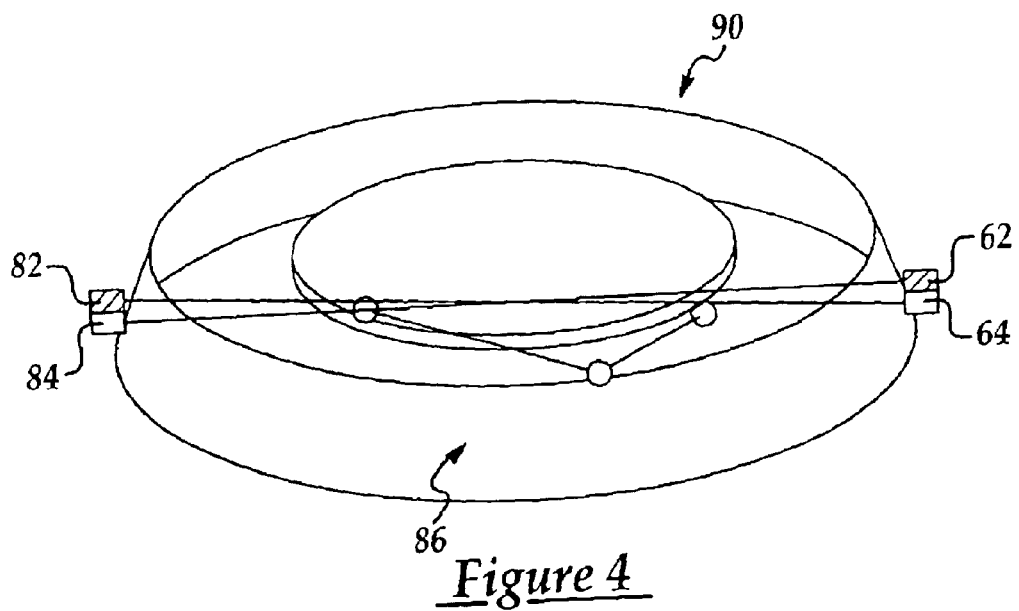
FIG. 4 depicts a pictorial diagram illustrating a photoresist cup and a laser generator and detection system that may be implemented in accordance with a preferred embodiment of the present invention.

FIG. 4 depicts a pictorial diagram 90 illustrating a photoresist (PR) cup 86 and a laser generator and detection system that may be implemented in accordance with a preferred embodiment of the present invention. Note that in FIGS. 3 and 4, like parts are indicated by identical reference numerals. Thus, FIG. 4 depicts laser generator 62, laser detector 64, laser generator 82, and laser detector 84. PR cup 86 of FIG. 4 is analogous to PR cups 66 and 74 illustrated in FIG. 3. In fact PR cups 66 and 74 of FIG. 3 may comprise a single PR cup, such as PR cup 86 of FIG. 4. PR cup 86 may configured from a transparent material, such as, for example, quartz. The height of laser detectors 64, 84 and/or laser generators 62, 82 may be adjusted to detect resist mist. The number of laser generators/detectors set to catch and detect resist mist can also be decreased or increased. Thus, a plurality of laser generators/detectors may thus be implemented, in accordance with the method and system of the present invention.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is thus not intended to be exhaustive or to limit the scope of the invention. Many modifications and variations are possible in light of the above teaching without departing from scope of the following claims. It is contemplated that the use of the present invention can involve components having different characteristics. It is intended that the scope of the present invention be defined by the claims appended hereto, giving full cognizance to equivalents in all respects.

What is claimed is:

1. A method for detecting contaminants during a semiconductor fabrication operation involving a semiconductor coating device, said method comprising the steps of:

generating a beam of laser light from a laser light source attached to at least one coater cup associated with said semiconductor coating device utilized in said semiconductor fabrication operation, wherein said at least one coater cup is comprises a transparent material; and automatically terminating said semiconductor fabrication operation, in response to detecting said contaminants utilizing said beam of laser light, wherein said contaminants are scattered as a result of said semiconductor fabrication operation.

2. The method of claim 1 further comprising the step of: detecting contaminants utilizing said beam of laser light.

3. The method of claim 1 further comprising the step of: attaching a laser light source to said at least one coater cup associated with said semiconductor coating device.

4. The method of claim 1 wherein said coater cup comprises a photoresist (PR) cup.

5. The method of claim 1 wherein said laser light source comprises a laser generator comprising an edge emitting laser or a solid state semiconductor light emitter.

6. The method of claim 1 wherein said laser light source comprises a laser detector comprising an edge emitting laser or a solid state semiconductor light emitter.

7. The method of claim 1 wherein said laser light source comprises a laser generator integrated with a laser detector.

8. The method of claim 1 wherein said semiconductor fabrication operation comprises a wafer spin coating operation.

9. The method of claim 1 wherein said contaminant comprises dust.

10. The method of claim 1 wherein said contaminant comprises photoresist (PR) dust scattered as a result of a wafer spin coating operation.

11. The method of claim 1 further comprising the step of: detecting contaminants utilizing said beam of laser light, wherein said contaminants comprise an abnormal photoresist dust flow.

12. The method of claim 1 further comprising the step of: detecting contaminants utilizing at least one laser detector to detect said beam of laser light generated from said laser light source.

13. The method of claim 12 wherein said laser light source is generated by at least one laser generator.

14. The method of claim 1 wherein said transparent material comprises quartz.

15. The method of claim 1 wherein said transparent material comprises glass.

16. A system for detecting contaminants during a semiconductor fabrication operation involving a semiconductor coating device, said system comprising:
  a laser light source attached to at least one coater cup associated with said semiconductor coating device utilized in said semiconductor fabrication operation, wherein said laser light source generates a beam of laser light, wherein said at least one coater cup comprises a transparent material;
  a laser detector for detecting contaminants utilizing said beam of laser light, such that said contaminants are scattered as a result of said semiconductor fabrication operation; and
  wherein said semiconductor fabrication operation is automatically terminated, in response to detecting said contaminants utilizing said beam of laser light.

17. The system of claim 16 wherein said coater cup comprises a photoresist (PR) cup.

18. The system of claim 16 wherein said laser light source comprises a laser generator comprising an edge emitting laser or a solid state semiconductor light emitter.

19. The system of claim 16 wherein said laser light source comprises a laser detector comprising an edge emitting laser or a solid state semiconductor light emitter.

20. The system of claim 16 wherein said laser light source comprises a laser generator integrated with a laser detector.

21. The system of claim 16 wherein said semiconductor fabrication operation comprises a wafer spin coating operation.

22. The system of claim 16 wherein said contaminant comprises dust.

23. The system of claim 16 wherein said contaminant comprises photoresist (PR) dust scattered as a result of a wafer spin coating operation.

24. The system of claim 16 wherein said contaminants comprise an abnormal photoresist dust flow.

25. The system of claim 16 wherein said contaminants are detectable utilizing at least one laser detector to detect said beam of laser light generated from said laser light source.

26. The system of claim 25 wherein said laser light source is generated by at least one laser generator.

27. The method of claim 16 wherein said transparent material comprises quartz.

28. The method of claim 16 wherein said transparent material comprises glass.

29. A system, comprising:
  a plurality of photoresist cups associated with a semiconductor coating device for use in a semiconductor fabrication operation, wherein said plurality of photoresist cups comprises a transparent material;
  at least one laser light source attached to each photoresist cup of said plurality of photoresist cups, wherein said at least one laser light source comprises a laser generator integrated with a laser detector;
  wherein said laser detector detects contaminants utilizing at least one beam of laser light generated by said laser light source, such that said contaminants are scattered as a result of said semiconductor fabrication operation; and
  wherein said semiconductor fabrication operation is automatically terminated, in response to detecting said contaminants utilizing said at least one beam of laser light.

30. The system of claim 29 wherein said at least one laser light source comprises an edge emitting laser or a solid state semiconductor light emitter and wherein said transparent material comprises quartz or glass.

* * * * *